United States Patent
Wei et al.

(10) Patent No.: US 10,758,580 B2
(45) Date of Patent: *Sep. 1, 2020

(54) COMPOSITION OF SEA BUCKTHORN PULP OIL AND PANAX NOTOGINSENG SAPONINS FOR TREATING OSTEOPOROTIC FRACTURE AND/OR OSTEOARTHRITIS AND USES THEREOF

(71) Applicant: SHAANXI TIANKUI BIOMEDICINE TECHNOLOGY LIMITED COMPANY, Xi'an (CN)

(72) Inventors: Xiazhen Wei, Xi'an (CN); Lanlan Song, Xi'an (CN); Shaohua Han, Xi'an (CN)

(73) Assignee: SHAANXI TIANKUI BIOMEDICINE TECHNOLOGY LIMITED COMPANY, Xi'an (CN)

(*) Notice: Subject to any disclaimer, the term of this patent is extended or adjusted under 35 U.S.C. 154(b) by 46 days.

This patent is subject to a terminal disclaimer.

(21) Appl. No.: 15/862,746

(22) Filed: Jan. 5, 2018

(65) Prior Publication Data

US 2018/0125907 A1 May 10, 2018

Related U.S. Application Data

(63) Continuation of application No. PCT/CN2016/088427, filed on Jul. 4, 2016.

(30) Foreign Application Priority Data

Jul. 6, 2015 (CN) .......................... 2015 1 0390865

(51) Int. Cl.

| A61K 36/185 | (2006.01) |
|---|---|
| A61K 36/258 | (2006.01) |
| A61P 19/02 | (2006.01) |
| A61P 19/08 | (2006.01) |

(52) U.S. Cl.
CPC .......... *A61K 36/258* (2013.01); *A61K 36/185* (2013.01); *A61P 19/02* (2018.01); *A61P 19/08* (2018.01)

(58) Field of Classification Search
None
See application file for complete search history.

(56) References Cited

U.S. PATENT DOCUMENTS

| 2009/0169623 A1* | 7/2009 | Sene | ...................... | A23L 33/105 |
| | | | | 424/474 |
| 2018/0161383 A1* | 6/2018 | Wei | ...................... | A61K 36/185 |

FOREIGN PATENT DOCUMENTS

| CN | 1679704 | * 10/2005 |
| CN | 1781510 | * 6/2006 |

OTHER PUBLICATIONS

Fatima T. et al. Fatty Acid Composition of Developing Sea Buckthorn Berry and the Transcriptome of the Mature Seed. PLoS One 7 (4)1-18, Apr. 2012. (Year: 2012).*
Liu, L. et al. Panax notoginseng Saponins Promotes Stroke Recovery by Influencing Expression of Nogo-A, NgR and p75NGF, In vitro and In vivo. Biological & Pharmaceutical Bulletin 37(4)560-568, 2014. (Year: 2014).*
Xu, Q. et al. Pharmacokinetics and Bioavailability of Ginsenoside Rb1 and Rg1 from Panax notoginseng in Rats. J of Ethnopharmacology 84:187-192, 2003. (Year: 2003).*

* cited by examiner

*Primary Examiner* — Ralph J Gitomer
(74) *Attorney, Agent, or Firm* — Wayne & Ken, LLC; Tony Hom

(57) ABSTRACT

The present disclosure discloses a natural pharmaceutical composition for treating osteoporotic fracture and/or osteoarthritis and an application thereof. The composition is composed of 73.3 wt %-98.3 wt % of sea buckthorn pulp oil and 1.7 wt %-26.7 wt % of *panax notoginseng* saponins. The composition can be further used for preventing and treating ostealgia diseases.

4 Claims, No Drawings

COMPOSITION OF SEA BUCKTHORN PULP OIL AND PANAX NOTOGINSENG SAPONINS FOR TREATING OSTEOPOROTIC FRACTURE AND/OR OSTEOARTHRITIS AND USES THEREOF

TECHNICAL FIELD

The present disclosure belongs to the technical field of researches of compatible dose-response and action purposes of natural drug formulas, and specifically relates to a natural pharmaceutical composition for treating osteoporotic fracture and/or osteoarthritis and an application thereof.

BACKGROUND

Osteoporosis is a systemic metabolic bone disease characterized by increase of bone fragility and easiness of fracture due to a decrease in bone mass and damage to a bone micro-architecture. Osteoporotic fracture is the most serious consequence of the osteoporosis. Fracture caused by the osteoporosis is fragility fracture. Due to a decrease in bone strength, a nonviolent action in daily life may cause fracture, and such a fracture belongs to complete fracture and has a high prevalence rate in old people. Common fracture parts are thoracolunbar spine, proximal humerus and distal radius, and multiple fracture may occur at hips, centrums and other parts of the old people, thereby resulting in an obvious increase of disability rate and case fatality rate.

With respect to the osteoporotic fracture, a three-drug therapeutic solution is adopted in clinical treatment. A diagnosis and treatment guideline of clinicians for preventing and treating osteoporotic fracture in American 2008 version points out "the first three anti-osteoporosis drugs after fracture" (anti-osteoporosis "triple combination" drugs) as follows: ① a calcium preparation is used, and a calcium amount is 800-1200 mg/d; ② an active vitamin D3 is used, 0.25-0.5 µg/d; and ③ calcitonin is used, 50 U/d, subcutaneous or intramuscular injection, nasal spray 200 U/d; or ③ an alendronate preparation is used. A combined application of the calcium preparation and a vitamin D drug is used as a basic drug for treating the osteoporosis by World Health Organization (WHO). A three-drug therapy (i.e. calcium+active vitamin D3+calcitonin/phosphate) is clinically used in general for a patient suffering from serious osteoporosis. The three-drug therapeutic solution is a common solution for treating the osteoporotic fracture at present.

However, with the adoption of the three-drug therapeutic solution, a contradiction between a compatible dose and an efficacy threshold of the three drugs may exist due to difficulty in mastering clinical individual differences, so the three drugs present various side effects in clinical application. For example, if the active vitamin D3 is taken for a long time in a great amount, hypercalcemia may be caused, and even symptoms such as anorexia, emesis, diarrhea, soft tissue heterotopic ossification and the like occur. Small-dose taking of the calcitonin is effect and relatively safe, and when large-dose calcitonin is used for short-term treatment, secondary hypothyroidism may be easily caused in a few patients. For poisoning patients after overdose, symptoms such as anorexia, weakness, nausea, emesis, diarrhea, diuresis, headache and thirst may occur, concentrations of calcium and phosphorus in blood and urine may be increased, and even hypertension and renal failure may be caused. For alendronate, common gastric irritation symptoms may be caused, such as nausea, emesis, stomachache, retrosternal pain, dyspepsia, pharyngalgia, odynophagia, chest stuffiness, dizziness, slight liver and kidney function change and the like.

In addition, chemical synthetic drugs, such as estrogen, progestational hormone, androgen, vitamin D, calcitonin and the like, are mainly used for preventing and treating the osteoporosis of women after menopause. A clinical parathyroid hormone (PTH) intermittent small-dose medication has an effect of inducing bone formation. A diphosphonate preparation is applied to achieve effects of inhibiting interfacial bone absorption and relatively increasing periprosthetic BMD. Side effects of different degrees may be caused in clinical curative effects for the application of the above drugs.

SUMMARY

In order to overcome defects in the prior art, a purpose of the present disclosure is to provide a natural pharmaceutical composition for treating osteoporotic fracture and/or osteoarthritis and an application thereof. The natural pharmaceutical composition is appropriate in compatibility, safe in dose and obvious in effects and can effectively solve problems that the existing Chinese and chemical synthetic drugs have side effects and poor curative effects in treating the osteoporotic fracture and/or the osteoarthritis.

The present disclosure is realized through the following technical solutions:

A natural pharmaceutical composition for treating osteoporotic fracture and/or osteoarthritis comprises the following components in percentage by mass: 73.3%-98.3% of sea buckthorn pulp oil and 1.7%-26.7% of *panax notoginseng* saponins.

The composition comprises the following components in percentage by mass: 93.4% of the sea buckthorn pulp oil and 6.6% of the *panax notoginseng* saponins.

The natural pharmaceutical composition is compounded by using the sea buckthorn pulp oil and the *panax notoginseng* saponins as active ingredients and can be prepared into soft capsules or oral liquid preparations, wherein the sea buckthorn pulp oil is extracted from fresh sea buckthorn fruits without seeds, and the *panax notoginseng* saponins is extracted from a cutting site and rhizomes of *panax notoginseng*.

A mass ratio of hexadecylenic acid to hexadecanoic acid contained in the sea buckthorn pulp oil is (1.02-1.1):1; or a mass ratio of the hexadecanoic acid to the hexadecylenic acid is (1.02-1.1):1. A mass ratio of panaxoside Rg1 to panaxoside Rb1 contained in the *panax notoginseng* saponins is 1:1.

The present disclosure further discloses an application of the natural pharmaceutical composition in preparation of a drug and/or health care product for treating the osteoporotic fracture and/or the osteoarthritis.

The drug and/or the health care product is a drug and/or health care product for regulating a metabolic balance of osteoclasts and osteoblasts.

The natural pharmaceutical composition can synthesize or produce signal molecules of epoxyeicosatrienoic acids in vivo. The signal molecules regulate the metabolic balance of the osteoclasts and the osteoblasts by virtue of positive and negative regulating pathways of protein signal molecules for activating bone reconstruction of an organism.

The drug and/or the health care product is a drug and/or health care product capable of inhibiting excessive secretions of the osteoclasts by decreasing the contents of alkaline phosphatase ALP, interleukin IL-1 cytokine, interleukin IL-6 cytokine and parathyroid hormone PTH.

Or the drug and/or the health care product is a drug and/or health care product capable of promoting secretion of the osteoblasts, promoting bone reconstruction and increasing a bone form reconstruction index by increasing the contents of bone gla protein BGP, calcitonin CT, osteoprotegerin OPG, estrogen E2, dehydroepiandrosterone DHEA, insulin-like growth factors DHEA and anandamide AEA.

The drug and/or the health care product is a drug and/or health care product capable of promoting secretion of the osteoblasts and increasing the bone form and bone reconstruction indexes by promoting the increase of cytochrome C oxidase COX, membrane permeability MPTP, membrane potentials MMP, hematopoietic iron-sulfur proteins Fe—S, hematopoietic iron proteins MttF, insulin-like growth factors IGF-1, transforming growth factors TGF-β, thrombopoietin TPO and erythropoietin EPO.

Or the drug and/or the health care product is a drug and/or health care product capable of inhibiting the secretions of the osteoclasts, promoting the secretions of the osteoblasts and increasing the bone form and bone reconstruction indexes by decreasing the contents of hematopoietic negative cytokines IL-1 and interleukin-6.

The drug and/or the health care product is a drug and/or health care product capable of inhibiting occurrence and development of inflammatory factors of the osteoarthritis by decreasing the contents of nitric oxide NO, histamine HIS, leukotrienes LT and malondialdehyde MDA in serum.

Or the drug and/or the health care product is a drug and/or health care product capable of inhibiting bone pain caused by the inflammatory factors by increasing the contents of β-endorphin β-EP and preprotachykinin β-PPT in vivo.

Compared with the prior art, the present disclosure has the following beneficial technical effects.

The natural pharmaceutical composition for treating the osteoporotic fracture and/or the osteoarthritis disclosed in the present disclosure is composed of the sea buckthorn pulp oil and the *panax notoginseng* saponins serving as the active ingredients according to a certain ratio (73.3%-98.3% of the sea buckthorn pulp oil and 1.7%-26.7% of the *panax notoginseng* saponins). The pharmaceutical composition can be converted into the poxyeicosatrienoic acids in vivo, and can activate multi-path molecular signal pathways in vivo such as proteins, cyclic nucleotides, calcium ions and the like or directly act on fatty acid-binding proteins, thereby achieving effects of vasodilating blood vessels, diminishing inflammation, promoting neovascularization, inhibiting cell migration or proliferation, promoting release of polypeptide hormones, promoting expressions of hematopoietic proteins and regulating the calcium signal pathway (capable of increasing intestinal calcium absorption and decreasing urinary calcium excretion). It is verified through experiments that the natural pharmaceutical composition can regulate and treat the osteoporotic fracture of an osteoporotic fracture model rate caused by a disproportion of content of cyclic nucleotide protein kinase signal molecules and a disproportion of content of endocrine hormones, immunogens and neurotransmitters.

In the present disclosure, through a dose-efficacy screening test of the natural pharmaceutical composition as well as medication verifications together with a positive drug diethylstilbestrol group and a Xianling Gubao capsule group under the same condition, and also through comparison with a model group, a normal group (sham-operated group) and a young group, the natural pharmaceutical composition in the present disclosure is proved to achieve effects on increasing a bone density and bone form (including femoral morphology, vertebrae morphology and tibia morphology) of ovariectomized female rats, increasing the content of estrogen E2, bone glaprotein (BGP), calcitonin (CT) and insulin-like growth factor (IGF-1) in serum of the ovariectomized female rats, decreasing the content of immune cytokine interleukin-1 (IL-1), immune cytokine interleukin-6 (IL-6) and hydroxyproline in serum of rats in a model medication group, increasing urine creatinine of the ovariectomized female rats and decreasing urinary calcium value. In the present disclosure, by virtue of a model with enhanced nociceptor-induced pain inflammation by enabling a "papain-induced rat osteoarthritis" simulated inflammatory mediator stimulus to intrude knee joint tissues, the low-dose group of the natural pharmaceutical composition in the present disclosure can obviously improve and eliminate inflammatory cells in synovial joint fluid of the knees on female and male rats.

The natural pharmaceutical composition in the present disclosure is superior to similar Chinese and chemical synthetic drugs for treating the osteoporotic fracture in the market, such as diethylstilbestrol, calcium gluconate, Xianling Gubao capsules and the like, in aspects of component ratios, doses and curative effects. Although the natural pharmaceutical composition has the same osteogenesis effect as the alendronate but is superior to alendronate drugs in pressure resistance and tenacity, and has an effect of resisting osteosclerosis (fragility fracture) and the like, which can obviously solve problems that the existing traditional Chinese medicine and chemical synthetic drugs have slow curative effects or unobvious curative effects and side effects and the like in treatment of osteoporotic fracture diseases. The natural pharmaceutical composition is applicable to treatment of a preclinical phase (also called a bone mass loss phase) and a clinical phase (an occurrence phase of fragility fracture) of the osteoporosis. The natural pharmaceutical composition is used for preventing and treating bone mineral loss, osteoporosis and compression fracture on hips and lumbar vertebra of women and men, increasing the bone density, repairing and reconstructing structural strength of the bone, improving and treating osteoarthritis and lumbago and back pain caused by the osteoporosis and obviously improving and treating osteoporosis fractures of women after menopause, senility caused by weakness and immunocompromise of men, and waist and knee pain of bone mineral loss and osteoporotic fracture caused by pathological secondary disease reasons, and has obvious treatment effects on symptoms such as hunch, spasm of lower limbs, weakness, insomnia and dreaminess and the like.

DETAILED DESCRIPTION

The present disclosure is further described in detail below in combination with specific embodiments. The description is an explanation of, not a limitation to, the present disclosure.

1. Preparation Method of Formula Ingredients, Formula Ratio Range and Daily Dose-Response Ratio The natural pharmaceutical composition for treating osteoporotic fracture and/or osteoarthritis disclosed in the present disclosure is a drug prepared from the following active ingredients in percentage by mass: 73.3%-98.3% of sea buckthorn pulp oil and 1.7%-26.7% of *panax notoginseng* saponins.

Specifically, a composition of 93.4% of the sea buckthorn pulp oil and 6.6% of the *panax notoginseng* saponins has an optimal effect.

Three preparation methods of the active ingredients in the present disclosure can be adopted as follows:

1) preparation of the sea buckthorn pulp oil, comprising common methods as follows:

① centrifugal separation by physical pressing:

pressing fresh mature sea buckthorn fruits (without seeds) through a pneumatic screw rod to obtain sea buckthorn juice and sea buckthorn fruit pulp residues, adding warm water of 50-55° C. into the fruit pulp residues for soaking 2-3 times, soaking for 60 min, performing centrifugal separation for different times, and purifying to obtain the sea buckthorn pulp oil with an oil extraction rate of 0.07%-4.0% (g/g);

② $CO_2$ supercritical extraction:

performing $CO_2$ supercritical extraction on the sea buckthorn fruit pulp residues obtained from the fresh mature sea buckthorn fruits (without seeds); industrial production extraction conditions are as follows: an extraction pressure of 35 MPa, an extraction temperature of 45° C., extraction time of 1.5 h, and a separation temperature of 45° C.; the oil extraction rate can reach 5.2% (g/g); steps are as follows: adding water according to a ratio of 1:1 to hydrate and remove impurities, adding 3%-5% of argil to discolor, and performing centrifugal dehydration, thereby obtaining 86% (g/g) of purified and refined sea buckthorn pulp oil; and ③ extraction with an n-hexane solvent:

moderately soaking dried sea buckthorn fruits, and extruding the fruits (removing the seeds) by a roller to obtain the fruit pulp residues; drying at constant temperature of 45° C., enabling the sea buckthorn fruit pulp residues to reach a granularity of 40 meshes, extracting with the n-hexane solvent, extracting for 50 minutes according to a ratio 1:8 of the material to the solvent at an extraction temperature of 60° C., and reaching a sea buckthorn fruit oil extraction rate of 5.2% (g/g); and purifying and refining, thereby obtaining 85% (g/g) of purified and refined sea buckthorn pulp oil.

The sea buckthorn pulp oil contains myristic acid C14:0, palmitic acid C16:0, palmitoleic acid C16:1, heptadecanoic acid C17:0, oleic acid C18:1, linoleic acid C18:2, linolenic acid C18:3, arachidic acid arachidic acid C20:0, β-sitosterol, stigmasterol, seed phytosterol, ergosterol, diterpene ester, triterpene ester, sterol ester, β-carotene, xanthophylls, quercetin kaempferol, isorhamnetin, vitamin E, vitamin K and other special components.

2) Preparation of the *panax notoginseng* saponins:

traditional alcohol extraction of the *panax notoginseng* saponins:

preparing effective parts of rhizomes and cutting site of *panax notoginseng* into 60-mesh *panax notoginseng* powder, performing reflux extraction with 70% of ethanol solution according to a ratio of 1:7 of the material, performing boiling reflux extraction twice, extracting for 1.5 hours each time, merging filtrate to reach a rate of 9.6% (g/g), concentrating through HPD-400 macroporous resin, eluting with 80% of ethanol, concentrating and drying the eluent, thereby obtaining the purified *panax notoginseng* saponins product. The *panax notoginseng* saponins contains panaxoside Rb1, panaxoside Rb2, panaxoside Rc, panaxoside Rd, panaxoside Rh2, panaxoside Re, panaxoside Rg1, panaxoside Rg2, panaxoside Rh1 and *panax notoginseng* saponin R1.

3) Formula preparation solution

① Content of pharmacodynamic fatty acids in compound sea buckthorn pulp oil and *panax notoginseng* saponins in the present disclosure must be as follows:

a content ratio (g/g) of hexadecylenic acid and hexadecanoic acid, in the sea buckthorn pulp oil is (1.02-1.1):1; or a content ratio (g/g) of the hexadecanoic acid to the hexadecylenic acid in the sea buckthorn pulp oil is (1.02-1.1):1; and a content mass ratio of Rg1 to Rb1 (mg/mg) of the *panax notoginseng* saponins is 1:1.

After compatible medication, the compound drug in the given range in the present disclosure can produce signal molecules of a symbolic biotransformation metabolite of epoxyeicosatrienoic acid (11,12-EETs)(ng/ml) in vivo, and the signal molecules can regulate a metabolic balance of osteoclasts and osteoblasts by virtue of positive and negative regulating pathways of protein signal molecules for activating bone reconstruction of an organism. Moreover, content of the in-vivo signal molecules of the epoxyeicosatrienoic acid (11,12-EETs)(ng/ml) is in close positive correlation with bone reconstruction.

② Preparation solution

Embodiment 1

A natural pharmaceutical composition for treating osteoporotic fracture and/or osteoarthritis is a drug prepared from the following active ingredients in percentage by mass: 94.6% of sea buckthorn pulp oil and 5.4% of *panax notoginseng* saponins.

Embodiment 2

A natural pharmaceutical composition for treating osteoporotic fracture and/or osteoarthritis is a drug prepared from the following active ingredients in percentage by mass: 87.2% of sea buckthorn pulp oil and 12.8% of *panax notoginseng* saponins.

Embodiment 3

A natural pharmaceutical composition for treating osteoporotic fracture and/or osteoarthritis is a drug prepared from the following active ingredients in percentage by mass: 74.6% of sea buckthorn pulp oil and 25.4% of *panax notoginseng* saponins.

Embodiment 4

A natural pharmaceutical composition for treating osteoporotic fracture and/or osteoarthritis is a drug prepared from the following active ingredients in percentage by mass: 93.4% of sea buckthorn pulp oil and 6.6% of *panax notoginseng* saponins (prepared according to a weight ratio of 15:1).

Embodiment 5

A natural pharmaceutical composition for treating osteoporotic fracture and/or osteoarthritis is a drug prepared from the following active ingredients in percentage by mass: 97.4% of sea buckthorn pulp oil and 2.6% of *panax notoginseng* saponins.

Embodiment 6

A natural pharmaceutical composition for treating osteoporotic fracture and/or osteoarthritis is a drug prepared from the following active ingredients in percentage by mass: 98.3% of sea buckthorn pulp oil and 1.7% of *panax notoginseng* saponins.

According to the preparation solutions of the natural pharmaceutical composition in one or more embodiments of the present disclosure, under preparation conditions of a total combination amount of the sea buckthorn pulp oil and the *panax notoginseng* saponins according to the mass ratio, 3%-6% of auxiliary material beewax is added, fine powdered *panax notoginseng* saponins and the sea buckthorn pulp oil are mixed and ground, a fineness of the fine *panax notoginseng* powder is controlled to be 30-50 (um) under a strong dispersion effect of a colloid mill at a rotating speed (2900 r/min-3600 r/min), and the *panax notoginseng* powder can be uniformly dispersed in the sea buckthorn pulp oil to prepare a compound preparation.

③ Effective dose range, daily dose and medication cycle of a compound composition An effective dose range of a natural pharmaceutical composition for treating osteoporotic fracture and/or osteoarthritis is as follows.

A composition ratio of drugs sea buckthorn pulp oil to *panax notoginseng* saponins is (mass/mass) % (g/g):

An efficacy formula ratio of an animal rat is:

A ratio of the sea buckthorn pulp oil to the *panax notoginseng* saponins is in a range of (73.3%-98.3%): (26.7%-1.7%);

A daily dose range of the animal rat is that sea buckthorn pulp oil and *panax notoginseng* saponins is equal to (3.6-0.17)+(0.2-0.02) g/kg.

A dose-response daily dose of an optimized group of the daily dose of the animal rat is as follows: a mass ratio of the sea buckthorn pulp oil to the *panax notoginseng* saponins is preferably 93.4%:6.6%. The ratio of the sea buckthorn pulp oil to the *panax notoginseng* saponins or a compatible weight ratio is preferably 15:1, and the daily dose is that the sea buckthorn pulp oil and the *panax notoginseng* saponins is equal to 1.2+0.08 g/kg.

A human clinical equivalent formula ratio is as follows:

a ratio of the sea buckthorn pulp oil to the *panax notoginseng* saponins is in a range of (73.4%-98.3%):(26.6%-1.7%);

a human daily dose range is that the sea buckthorn pulp oil and the *panax notoginseng* saponins is equal to (26-2.7)+(2.6-0.17) g/kg.

A dose-response daily dose of an optimized group of the human clinical equivalent daily dose is that a mass ratio of the sea buckthorn pulp oil to the *panax notoginseng* saponins is preferably 93.4%:6.6%. The ratio of the sea buckthorn pulp oil to the *panax notoginseng* saponins or a compatible weight ratio is preferably 15:1, and the daily dose is that the sea buckthorn pulp oil and the *panax notoginseng* saponins is equal to 12+0.8 g/60 kg.

A treatment cycle of the present compound drug for treating osteoporotic fracture and/or osteoarthritis is 4 months.

2. Symbolic Indexes for Verifying Treatment of the Osteoporotic Fracture and/or the Osteoarthritis.

1) Production of the signal molecules of the symbolic biotransformation metabolite of epoxyeicosatrienoic acid (11,12-EETs)(ng/ml): after taken by the rat and a human body, the compound drug in the given range in the present disclosure can produce the signal molecules of the symbolic biotransformation metabolite of epoxyeicosatrienoic acid (11,12-EETs)(ng/ml) in vivo, and the signal molecules can regulate the metabolic balance of the osteoclasts and the osteoblasts by virtue of the positive and negative regulatory pathways of the protein signal molecules for activating bone reconstruction of the organism. Moreover, the content of the signal molecules of the epoxyeicosatrienoic acid (11,12-EETs)(ng/ml) is in close positive correlation with the bone reconstruction.

2) Comparison of medication results with a positive control drug group, a model group and a normal group: medication verifications are performed on a dose-efficacy screening test of the compound drug, a model group, a normal group (sham-operated group), a young group and positive drug groups (diethylstilbestrol, Xianling Gubao capsules and a chemical synthetic drug alendronate sodium) under the same condition, and the following obvious characteristic effects are achieved.

① Comparison with an osteoporotic fracture model group, the natural pharmaceutical composition can improve the bone density and bone form of ovariectomized female rats.

When the natural pharmaceutical composition in the present disclosure is taken for 3 months, the bone density of tibia of the rats is increased by 15.26 $g/m^2$, the bone density of lumbar vertebra is increased by 7.2 $g/m^2$, the bone density of thighbone is increased by 9.2 $g/m^2$, density of bone cortex is increased by 6.4 $g/m^2$, and a thickness of the bone cortex is increased by 0.14 mm. The natural pharmaceutical composition is better than the positive drug such as the diethylstilbestrol group and the Xianling Gubao capsule group, and has functional parameters close to those in the normal group, and has obvious statistical significance on the curative effect ($P<0.01$) compared with the model group.

② Comparison with the osteoporotic fracture model group, the natural pharmaceutical composition can improve bone form of thighbone of the ovariectomized female rats.

A bone trabecula percentage of the thighbone is increased by 9.52% (Tbr), and a bone trabecula width of the thighbone is increased by 31.1 Tb.Wi (um), and a quantity of bone trabeculas of the thighbone is increased by 1.4/mm, and a separation degree of the bone trabeculas of the thighbone (i.e., a mean width of the bone medullary cavity among the bone trabeculas) is decreased by 747.32 Tb.sp (um). The natural pharmaceutical composition is better than the positive drug such as the diethylstilbestrol group and the Xianling Gubao capsule group, has functional parameters close to those in the normal group, and has obvious statistical significance on curative effect ($P<0.01$) compared with the model group.

③ Comparison with the osteoporotic fracture model group, the natural pharmaceutical composition can improve bone form of vertebra of the ovariectomized female rats.

A bone trabecula percentage of the vertebra is increased by 12.5% (Tbr), and a bone trabecula width of the vertebra is increased by 10.17 Tb.Wi (um), and a quantity of bone trabeculas of the vertebra is increased by 1.43/mm, and a separation degree of the bone trabeculas of the vertebra (i.e., a mean width of the bone medullary cavity among the bone trabeculas) is decreased by 86.14 Tb.sp (um). The natural pharmaceutical composition is better than the positive drug such as the diethylstilbestrol group and the Xianling Gubao capsule group, has functional parameters close to those in the normal group, and has obvious statistical significance on the curative effect ($P<0.01$) compared with the model group.

④ Comparison with the osteoporotic fracture model group, the natural pharmaceutical composition can improve bone form of tibia of the ovariectomized female rats.

A bone trabecula percentage of the tibia is increased by 13.9% (Tbr), and a bone trabecula width of the tibia is increased by 8.0 Tb.Wi (um), and a quantity of bone trabeculas of the tibia is increased by 1.79/mm, and a separation degree of the bone trabeculas of the tibia (i.e., a mean width of the bone medullary cavity among the bone trabeculas) is decreased by 747 Tb.sp (um). The natural pharmaceutical composition is better than the positive drug such as the diethylstilbestrol group and the Xianling Gubao capsule group, and the above functional parameters have obvious statistical significance on the curative effect (P<0.01 or P<0.05) compared with the model group.

⑤ Compared with the osteoporotic fracture model group, the natural pharmaceutical composition can increase content of estrogen E2 by 43% (pmol/ml), and increase a content of a sex hormone conversion product of dehydroepiandrosterone DHEA by 50% (ug/ml) and decrease a content of parathyroid hormone PTH by 24% (pg/ml) in serum of the ovariectomized female rats; and regarding to the natural pharmaceutical composition, a ratio of two hormones of (disordered) E2 and PTH is adjusted from 2:1 to 1:1 (healthy and normal). The natural pharmaceutical composition is better than the positive drug such as the diethylstilbestrol group and the Xianling Gubao capsule group, and the above functional parameters have obvious statistical significance on the curative effect (P<0.01 or P<0.05) compared with the model group.

⑥ Compared with the osteoporotic fracture model group, the natural pharmaceutical composition can increase a content of bone gla protein (BGP) by 51.7% (ng/ml), and increase calcitonin (CT) by 50.7% (pg/ml) and increase insulin-like growth factor (IGF-1) by 50.6% (pg/ml) in the serum of the ovariectomized female rats; and regarding to the natural pharmaceutical composition, a ratio of two hormones of (disordered) CT and BGP is adjusted from a ratio (2.1-2.2):1 to 1:1 (healthy and normal). The natural pharmaceutical composition is better than the positive drug such as the diethylstilbestrol group and the Xianling Gubao capsule group, and the above functional parameters have obvious statistical significance on the curative effect (P<0.01 or P<0.05) compared with the model group.

⑦ Compared with the osteoporotic fracture model group, the natural pharmaceutical composition can decrease content of immune cell cytokine interleukin-1 by 18.7% (pg/mL), decrease content of immune cell cytokine interleukin-6 by 21.4% (pg/mL) and decrease content of hydroxyproline by 16.1% (umol/mL) in serum of rats in the model medication group; regarding to the natural pharmaceutical composition, if the content values of the interleukin-1 and the interleukin-6 in the serum are increased at the same ratio (promoting bone absorption), the content value of the hydroxyproline is also increased at the same ratio (the substance is a metabolic end product of collagens); and the content values of the interleukin-1 and the interleukin-6 are in positive correlation with the hydroxyproline (a positive value of bone absorption, or a negative value of bone formation). The natural pharmaceutical composition is better than the positive drug such as the diethylstilbestrol group and the Xianling Gubao capsule group, and the above functional parameters have obvious statistical significance on the curative effect (P<0.01 or P<0.05) compared with the model group.

⑧ Compared with the osteoporotic fracture model group, the natural pharmaceutical composition can increase urine creatinine and decrease urinary calcium value of the ovariectomized female rats, and the urine creatinine value and the urinary calcium value of the ovariectomized female rat models are in negative correlation (i.e., the urinary creatinine value is decreased, urinary calcium excretion is increased, and bone calcium loss is high). The experimental drug of the present formula can obviously increase the urinary creatinine value by 19.2% and increase the urinary calcium excretion by 22%, and is better than the positive drug such as the diethylstilbestrol group and the Xianling Gubao capsule group. The above functional parameters have obvious statistical significance on the curative effect (P<0.01 or P<0.05) compared with the model group.

⑨ Compared with the osteoporotic fracture model group, the natural pharmaceutical composition can increase the content of osteoprotegerin OPG by 27.3% (pg/ml) in serum of ovariectomized female rats in a medication group; and a binding rate of the natural pharmaceutical composition and a ligand RANKL is increased by 27% (pg/ml); and a ratio of the OPG to the RANKL is increased from 0.89 in a disorder state to 1.58, i.e., the receptor activator (RANK) of the occupying competitive cytokine KB of the glycoprotein receptor of osteoprotegerin OPG is bound with the ligand RANKL, and activation of binding of RANK/RANKL on signal transduction of the osteoclast is inhibited, thereby resisting occurrence and development of the osteoporosis.

⑩ The test drug group of the formula shows that the increase and the decrease of the alkaline phosphatase ALP (mmol/ml) in the serum are sensitivity indexes for diagnosing metabolisms of the osteoblasts or osteoclasts; when the osteoprotegerin OPG in the serum is increased, the content of the bone gla protein, the calcitonin and the estrogen is increased, then the ALP (mmol/ml) is decreased, and the ALP is in negative correlation with the osteoprotegerin, the bone gla protein, the calcitonin and the estrogen.

A model with enhanced nociceptor-induced pain inflammation by enabling a "papain-induced rat osteoarthritis" simulated inflammatory mediator stimulus to intrude knee joint tissues verifies that:

① analgesia influencing factors are increased. The natural pharmaceutical composition enables the test medication group of an inflammation model to increase content of β-endorphin of female rats by 17.2% (pg/ml), to increase the content of β-endorphin of male rats by 39.5% (pg/ml), to increase preprotachykinin of the female rats by 26% (pg/ml), and to increase the preprotachykinin of the male rats by 50% (pg/ml); and since the present natural pharmaceutical composition has a drug effect of increasing the analgesia influencing factors, occurrence and development of pathological injuries of bone joints may be effectively inhibited;

② inflammatory influencing factors are decreased. Compared with the model group, the test group of the natural pharmaceutical composition can decrease the content of nitric oxide NO of the female rats by 22% umol/L, decrease the content of the nitric oxide NO of the male rats by 14% umol/L, decrease the content of histamine of the female rat group by 30.4% (ug/L), decrease the content of the histamine of the male rat group by 26.4%, decrease the content of leukotrienes of the female rats by 25.33% (ng/L), decrease the content of the leukotrienes of the male rats by 28.40% (ng/L), decrease the content of interleukin-1 of the female rats by 15.4% (ng/L), decrease the content of the interleukin-1 of the male rats by 26.05% (ng/L), decrease a rate of clearing malondialdehyde MDA in serum of the female rats by 22.70% (nmol/L), and decrease a rate of clearing the malondialdehyde (MDA) in serum of the male rats by 35% (nmol/L).

By virtue of "count analysis of inflammatory cells in knee-joint synovial joint fluid" on female and male rats in the inflammation model group, it is shown that in the natural pharmaceutical composition, the female and male rats can be obviously improved in the low-dose group and the inflammatory cells in the knee-joint synovial joint fluid can be eliminated. Statistical analysis shows obvious significance, P<0.05; the natural pharmaceutical composition has obvious statistical significance P<0.01 on pathological sections of cartilage (thighbone part) of the female rats; and the natural pharmaceutical composition has obvious statistical significance P<0.05 on pathological sections of cartilage (the thighbone part) of the male rats.

The signal molecules of the epoxyeicosatrienoic acid produced by the formula of the natural pharmaceutical composition promote an improvement of a hematopoietic microenvironment.

Pathogenesis of the osteoporosis is injury of liver mitochondria membrane, causing a decrease of membrane permeability (MPTP) and membrane potential (MP), a decrease of mitochondrial hematopoietic iron-sulfur proteins and iron protein (Fe—S, MtF), ferrochelatase (FECH) and cytochrome oxidase (COX), a decrease of a positive hematopoietic cytokine interleukin-3 and a granulocyte-macrophage colony stimulating factor (GM-CSF), an increase of a negative hematopoietic cytokine interleukin-1 (IL-1), an increase of interleukin-6 (IL-6), a decrease of a hematopoietic cytokine (an insulin-like growth factor IGF-1), also called an osteoblast factor and a transforming growth factor (TGF-β), and a decrease of a hematopoietic specific cytokine-thrombopoietin (TPO) and erythropoietin (EPO) as direct reasons of causing the osteoporosis. The natural pharmaceutical composition in the present disclosure synthesizes and produces the signal molecules of the epoxyeicosatrienoic acid in vivo and synergistically promotes injury repair of the mitochondrial membrane, thereby promoting the increase of the membrane permeability (MPTP), the membrane potential (MMP), the mitochondrial hematopoietic iron-sulfur proteins and iron protein (Fe—S, MtF), the ferrochelatase (FECH) and the cytochrome oxidase (COX), the increase of the positive hematopoietic cytokine interleukin-3 and the granulocyte-macrophage colony stimulating factor (GM-CSF), the decrease of the negative hematopoietic cytokine interleukin-1 (IL-1), the decrease of the interleukin-6 (IL-6), the increase of the hematopoietic cytokine (the insulin-like growth factor IGF-1), also called the osteoblast factor and the transforming growth factor (TGF-β), and the increase of the hematopoietic specific cytokine-thrombopoietin (TPO) and the erythropoietin (EPO), so as to effectively resist the osteoporosis arthritis and bone pain diseases.

In conclusion, the natural pharmaceutical composition synthesizes or produces the signal molecules of the epoxyeicosatrienoic acid in vivo, and achieves a multi-path amplified effect of protein and calcium signal molecules synergistically with the original formula, and improves the hematopoietic microenvironment and other symbolic cytokine effects, and regulates internal secretion, and regulates a metabolic balance of the osteoclasts and osteoblasts and promotes the bone reconstruction, thereby effectively resisting or preventing and treating the osteoporotic fracture, the osteoarthritis and the bone pain diseases.

3. Clinical Observation of Clinical Effects of 60 Cases (Reference Drugs).

(1) General Information of Selected Cases:

① 80 cases are selected in the present experimental study, and 64 cases are completed, including 30 male cases and 34 female cases (5 expulsion cases and 11 exclusion cases).

② age distribution of patients: a male age range is 59.54±2.84, and a female age range is 57.65±2.68.

③ illness degrees of the patients 5 mild patients (7.81%), 18 moderate patients in the test group (28.13%) and 41 severe patients in the test group (64.06%).

(2) Determination of Clinical Biochemical Indexes.

1) Determination of Symbolic Bone Absorption Indexes of Deoxypyridinoline and Hydroxyproline.

Determination of bone absorption markers of females taking the drug for 6 months are as follows. The increase of the deoxypyridinoline and the hydroxyproline in urine of an osteoporosis patient can sensitively reflect an obvious increase of human osteoclast activity, i.e., bone absorption dominates, causing a decrease of bone mass, an acceleration of osteoclast bone dissolution, an increase of cortical porosity, a decrease of volumes of trabecular bones and cortical bones, a negative calcium balance, a calcium loss of bones and an obvious decrease of systemic bone mineral content and bone mineral density. A woman after menopause lacks of estrogen and increases the bone absorption, and DPD/Cr content of the woman after menopause is obviously higher than that of a woman before menopause. The DPD/Cr content in the urine is closely related to the osteoporosis. A measured value of the DPD/Cr content in the urine is a sensitivity indicator reflecting the bone absorption.

In clinical study, 34 female cases and 30 male cases suffering from the osteoporosis are respectively subjected to determination before human dose medication of the composition (the determination of the deoxypyridinoline and the hydroxyproline in the urine) and after medication (see Table 1-Table 2)

TABLE 1

Comparison of biochemical index level in urine of women taking the drug for 6 months

| Index | Number of Cases | Before medication | Medication within 6 months | Comparison within groups (6 months) t | p |
|---|---|---|---|---|---|
| Deoxy-pyridinoline | 34 | 220.377 ± 36.557 | 178.249 ± 29.580 | 35.128 | <0.001 |
| Hydroxy-proline | 34 | 29.171 ± 4.888 | 22.194 ± 3.939 | 16.852 | <0.001 |

Seen from Table 1, for women during medication within 6 months, the contents of the deoxypyridinoline and the hydroxyproline in the urine are obviously decreased. Through comparison within the groups before and after medication, P<0.001, and the difference has high statistical significance; and the novel composition has an effect of inhibiting osteoclast absorption for the female osteoporosis patients, thereby achieving an effect of preventing and treating the osteoporosis.

TABLE 2

Comparison of biochemical index level in urine of men taking the drug for 6 months

| Index | Number of Case | Before medication | Medication within 6 months | Compare within groups (6 months) t | P |
|---|---|---|---|---|---|
| Deoxy-pyridinoline | 30 | 238.826 ± 41.511 | 193.959 ± 33.463 | 30.465 | <0.001 |
| Hydroxy-proline | 30 | 32.718 ± 5.376 | 24.251 ± 6.552 | 16.968 | <0.001 |

Seen from Table 2, for men during medication within 6 months, the contents of the deoxypyridinoline and the hydroxyproline in the urine are obviously decreased. Through comparison within the groups before and after medication, and the difference has high statistical significance (P<0.001). The novel composition has an effect of inhibiting osteoclast absorption for the male osteoporosis patients, thereby achieving the effect of preventing and treating the osteoporosis.

2) Curative Effect Results of Traditional Chinese Medicine Symptoms

Clinical symptoms of the osteoporosis include: ache on the waist and back, waist weakness, spasm of lower limbs, trudge, weakness, dizziness and tinnitus, insomnia and dreaminess, intolerance of cold and pale skin.

①Comparison of various symptoms before and after the test

TABLE 3

Comparison of various symptoms within 4-6 months before and after the test

| symptoms | N | Before test | | | | After test | | | | Comparison within groups | |
|---|---|---|---|---|---|---|---|---|---|---|---|
| | | − | + | ++ | +++ | − | + | ++ | +++ | Z | P |
| Ache on waist and back | 64 | 0 | 5 | 18 | 41 | 7 | 39 | 16 | 2 | −8.224 | 0.000 |
| Waist weakness | | 0 | 18 | 21 | 25 | 18 | 39 | 5 | 2 | −7.327 | 0.000 |
| Spasm of lower limbs | | 2 | 23 | 28 | 11 | 32 | 27 | 5 | 0 | −7.301 | 0.000 |
| Trudge | | 14 | 18 | 23 | 9 | 35 | 22 | 7 | 0 | −4.985 | 0.000 |
| weakness | | 7 | 16 | 23 | 18 | 23 | 27 | 14 | 0 | −5.357 | 0.000 |
| Dizziness and tinnitus | | 5 | 23 | 27 | 9 | 32 | 32 | 0 | 0 | −7.287 | 0.000 |
| Insomnia and dreaminess | | 0 | 21 | 34 | 9 | 25 | 39 | 0 | 0 | −8.369 | 0.000 |
| Intolerance of cold | | 2 | 16 | 32 | 14 | 28 | 34 | 2 | 0 | −8.064 | 0.000 |
| Pale skin | | 0 | 0 | 36 | 28 | 28 | 34 | 2 | 0 | −9.92 | 0.000 |

Seen from Table 3, the various traditional Chinese medicine symptoms are obviously improved before the test and within 3-4 months after medication. Through comparison within the groups before and after the test, P<0.001, and the difference has high statistical significance.

② Integral comparison of traditional Chinese medicine symptoms before and after the test:

TABLE 4

Integral comparison of traditional Chinese medicine symptoms before the test and after experiments

| Test time | Cases | Integral before test | Integral after test | Comparison within groups | | |
|---|---|---|---|---|---|---|
| | | | | Difference | t | p |
| 4 months | 64 | 53.03 ± 12.93 | 20.33 ± 10.31 | 32.70 ± 8.06 | 32.465 | <0.001 |
| 6 months | 64 | 53.03 ± 12.93 | 9.95 ± 9.43 | 43.08 ± 10.08 | 31.909 | <0.001 |

Seen from Table 4, the mean integrals of the traditional Chinese medicine symptoms are obviously decreased in two groups after the test due to treatment of 4-6 months. Through comparison within the groups, P<0.001, and the difference has high statistical significance.

3) Determination of Bone Density:

Curative effect results of bone density of lumbar vertebra (L3), (L4) in the clinical experiment (6 months):

TABLE 5

Curative effects of bone density of lumbar vertebra 3 (L3) within 6 months after test

| Lumbar vertebra 3(L3) | n | Excellent n (%) | Effective n (%) | Inefficient n (%) | Total effective rate % |
|---|---|---|---|---|---|
| Female | 34 | 15(44.12) | 17(50.00) | 2(5.88) | 94.12 |
| Male | 30 | 6(18.18) | 24(81.82) | 0(0) | 100 |
| Integrated | 64 | 21(32.81) | 41(64.06) | 2(3.13) | 96.87 |

TABLE 6

Curative effects of bone density of lumbar vertebra 4 (L4) within 6 months after test

| Lumbar vertebra 4(L4) | n | Excellent n (%) | Effective n (%) | Inefficient n (%) | Total effective rate % |
|---|---|---|---|---|---|
| Female | 34 | 16(47.06) | 16(47.06) | 2(5.88) | 94.12 |
| Male | 30 | 16(53.33) | 14(46.67) | 0(0) | 100 |
| Integrated | 64 | 32(50.00) | 30(46.87) | 2(3.13) | 96.87 |

TABLE 7

Curative effect result table of total bone density of lumbar vertebra (L3, L4) within 6 months after test

| Lumbar vertebra (L1-L4) | n | Excellent n (%) | Effective n (%) | Inefficient n (%) | Total effective rate % |
|---|---|---|---|---|---|
| Female | 34 | 16(45.6) | 17(48.53) | 3(6) | 94.13 |
| Male | 30 | 14(46.67) | 16(53.33) | 0(0) | 100 |
| Integrated | 64 | 21(32.81) | 40(62.5) | 3(4.69) | 95.31 |

TABLE 8

Curative effect result table of total bone density of lumbar vertebra (L3, L4) within 6 months after test

| Lumbar vertebra (L1-L4) | n | Excellent n (%) | Effective n (%) | Inefficient n (%) | Total effective rate % |
|---|---|---|---|---|---|
| Female | 34 | 26(76.47) | 7(20.58) | 1(2.9) | 97 |
| Male | 30 | 27(90.00) | 3(10.00) | 0(0) | 100 |
| Integrated | 64 | 53(82.81) | 10(15.6) | 1(2.9) | 98.41 |

Seen from Table 4-Table 8, through medication of the drug formula within 4 months, the curative effects of clinical traditional Chinese medicine subjective symptoms of the osteoporosis have a significant difference due to statistical comparison before and after the test (P<0.01).

Results of a two-photon bone densitometry instrument show that: for women taking the drug for 6 months (treated in the first course of treatment), the marked effective rate of bone density of the lumbar vertebra (L3, L4) is 45.60%, and the total effective rate is 94.13%; and for men taking the drug for 6 months (treated in the first course of treatment), the marked effective rate of bone density of the lumbar vertebra (L3, L4) is 46.67%, and the total effective rate is 100%. In the second course of treatment during medication, the marked effective rates of the women and men are obviously increased. For women taking the drug for 6 months (treated in the second course of treatment), the marked effective rate of the bone density of the lumbar vertebra (L3, L4) is 76.47%, and the total effective rate is 97%; and for men taking the drug for 6 months (treated in the second course of treatment), the marked effective rate of the bone density of the lumbar vertebra (L3, L4) is 82.81%, and the total effective rate is 100%.

In conclusion, after the novel composition for treating the osteoporotic fracture is taken for 4-6 months and is used for treatment within 2 treatment cycles, general kidney-yang deficiency type (liver-kidney yin deficiency) osteoporotic fracture can be repaired, and a bone reconstruction treatment effect is achieved.

The natural pharmaceutical composition in the present disclosure can be converted into the signal molecules of the epoxyeicosatrienoic acid in vivo and can activate proteins, cyclic nucleotide, calcium and other multi-path molecular signal pathways to achieve a synergistic effect of amplifying the signal molecules, improve the hematopoietic microenvironment and effectively promote the increase of the content of the mitochondrial cytochrome oxidase COX, the mitochondrial membrane permeability (MPTP), the mitochondrial membrane potential (MMP), the mitochondrial hematopoietic iron-sulfur proteins (Fe—S), mitochondrial ferritin (MtF), the insulin-like growth factor (IGF-1), the transforming growth factor (TGF-β), the thrombopoietin (TPO) and the erythropoietin (EPO) and the decrease of the content of the negative hematopoietic cytokine interleukin-1 (IL-1) and the interleukin-6 (IL-6), thereby effectively preventing and treating the osteoporotic fracture, the osteoarthritis and the bone pain diseases.

The natural pharmaceutical composition can achieve effects of improving the hematopoietic microenvironment, regulating internal secretion, regulating the metabolic balance of the osteoclasts and osteoblasts, decreasing the alkaline phosphatase, increasing bone metabolism marker indexes such as the osteoprotegerin, the bone gla protein and the like in the serum, increasing the bone density of the thighbone, the tibia and the vertebra, obviously improving the bone form of bone reconstruction and symbolic indexes of bone biomechanics, and effectively preventing and treating the osteoporotic fracture, the osteoarthritis and the bone pain diseases. The natural pharmaceutical composition is scientific in compatibility, safe in dose, zero in side effect, fast in efficacy, obvious in treatment effects and better than similar Chinese and partially controlled chemical compound in the market.

The above embodiments are only for describing technical conceptions and characteristics of the present disclosure. The purpose of the present disclosure is to enable those skilled in the art to know and implement the content of the present disclosure, not intended to limit the protection scope of the present disclosure. All equivalent replacements or modifications made according to spirit of the present disclosure should be included in the protection scope of the present disclosure.

What is claimed is:

1. A composition for treating osteoporotic fracture and/or osteoarthritis, comprising: sea buckthorn pulp oil and *panax notoginseng* saponins;
    wherein a weight ratio of the sea buckthorn pulp oil to the *panax notoginseng* saponins is 15:1
    wherein the sea buckthorn pulp oil is extracted from fresh deseeded sea buckthorn fruits, and the *panax notoginseng* saponins is extracted from rhizomes of *panax notoginseng*.

2. A drug and/or health care product for treating osteoporotic fracture and/or osteoarthritis, wherein the drug and/or health care product is prepared from the composition as defined in claim 1.

3. A method for treating osteoporotic fracture and/or osteoarthritis, comprising: administrating to the patient an effective amount of the drug and/or health care product as defined in claim 2.

4. The composition of claim 1, wherein active ingredients in the sea buckthorn pulp oil comprises hexadecylenic acid (C16:1) and hexadecanoic acid (C16:0); and active ingredients in the *panax notoginseng* saponins comprises Rg1 and Rb1.

* * * * *